United States Patent [19]

Dory

[11] Patent Number: 4,727,875
[45] Date of Patent: Mar. 1, 1988

[54] GENERATOR OF HIGH POWER ELASTIC PULSES FOCUSED IN A LIQUID AND OBTAINED BY IMPACT

[76] Inventor: Jacques Dory, 91, rue des Molveaux, 77450 Coupvray Esbly, France

[21] Appl. No.: 880,369

[22] Filed: Jun. 30, 1986

[30] Foreign Application Priority Data

Jun. 28, 1985 [FR] France ................................ 85 09865

[51] Int. Cl.$^4$ .............................................. A61B 17/00
[52] U.S. Cl. .................................................. 128/328
[58] Field of Search .............. 128/24 A, 328; 181/121

[56] References Cited

U.S. PATENT DOCUMENTS 4,064,964 12/1977 Norden ................................ 181/121
4,506,758 3/1985 Fair .................................... 181/121

Primary Examiner—William E. Kamm
Assistant Examiner—J. P. Lacyk
Attorney, Agent, or Firm—William A. Drucker

[57] ABSTRACT

A high power elastic pulse generator is provided comprising an anvil to the emitting face of which is bonded an acoustic lens immersed in a liquid. A hammer is driven by an electromagnetic device and recalled by a spring.

10 Claims, 14 Drawing Figures

GENERATOR OF HIGH POWER ELASTIC PULSES FOCUSED IN A LIQUID AND OBTAINED BY IMPACT

BACKGROUND OF THE INVENTION

1. Field of the Invention

High power elastic waves propagated in a liquid are used for destroying solid structures. This is the case in particular with renal or vesicle calculi.

For the method to be usable on biological tissues, it is necessary to be able to focus the wave in a precise point, so as to limit the energy density outside the zone of use and to reduce the risks of damage to the tissues through which it passes.

Now, it is known that the dimension of the focal spot is proportional to the wave length of the elastic wave, so to the duration of the wave front.

It is therefore indispensable, so as to obtain efficient focusing, to work with very steep wave fronts of the order of a microsecond, In this case, for example, the energy may be concentrated in a diameter of the order of 3 mm.

2. Descriprion of the Prior Art

To solve the problem of the generation of very steep wave fronts, it has been proposed to use either pin point elastic wave sources or distributed sources.

The pin point sources are formed either by a microcharge fired in the water, the explosion of which generates a spherical wave, or, as disclosed in DE. No. 2 722 252 (DORNIER), by discharging an electric arc between two immersed electrodes.

In both cases, the spherical wave generated is concentrated by an elliptic mirror. These solutions give poor control of the power and of the form of the wave produced and cause rapid wear of the parts which they require. The reliability is low, because the very high intensity at the level of a pin point source causes the appearance of disturbing phenomena.

Distributed sources have a large area, all the points of which vibrate in phase for generating a plane wave, which is concentrated either with an acoustic lens or by giving to the source itself the shape of a spherical skull cap.

They have a priori the advantage of limited fatigue because the energy density on the surface of the source is much lower than at the focal point.

The invention relates to a device which belongs to this category.

High power distributed source generators are already known for instance from SOURCES OF HIGH-INTENSITY ULTRASOUND (Volume 1) by L. D. ROZENBERG, Plenum Press, New York, 1969, in which the source is formed by a mosaic of piezoelectric elements. Their disadvantage is that their area must be considerable, because the power provided by each element is relatively small and because the electric generators required for energizing the elements must reach instantaneous powers of the order of a megawatt, which leads to high costs.

The invention provides a high power distributed source generator of much simpler construction.

SUMMARY OF THE INVENTION

The generator of the invention comprises focusing means associated with a distributed elastic pulse source and is characterized in that said source is formed by an anvil and a hammer having two respective parallel facing faces and by means for propelling and returning the hammer bringing said faces alternately into contact at a speed of several meters per second and separating them from one another, in that the anvil has an emission face distinct from the impact face, in that the hammer comprises an impacting element of a few millimeters thickness, in that the propulsion means and the hammer are adapted so that, in a first stage, said impacting element is brought to a sufficient kinetic energy whereas said facing faces are separated by a small gap and in that, in a second stage much shorter than the first, said impacting element, uncoupled from the energy point of view from the propulsion means, travels over said gap under the effect of the kinetic energy accumulated so as to produce an impact with the anvil.

In another feature of the invention, the generator comprises sensors adapted for detecting the pressure wave fronts at respective points distributed at the periphery of the emitting face of the anvil; means for measuring the time shifts between the wave fronts received by the respective sensors and means for setting, as a function of the time shifts thus measured, screws for adjusting the slant of the anvil distributed at points spaced apart over a collar which surrounds the anvil, opposite the respective sensors.

BRIEF DESCRIPTION OF THE DRAWINGS

Other features and the advantages of the invention will be clear from the following description, with reference to the accompanying drawings in which.

DESCRIPTION OF THE PREFERRED EMBODIMENTS

Figure 1:
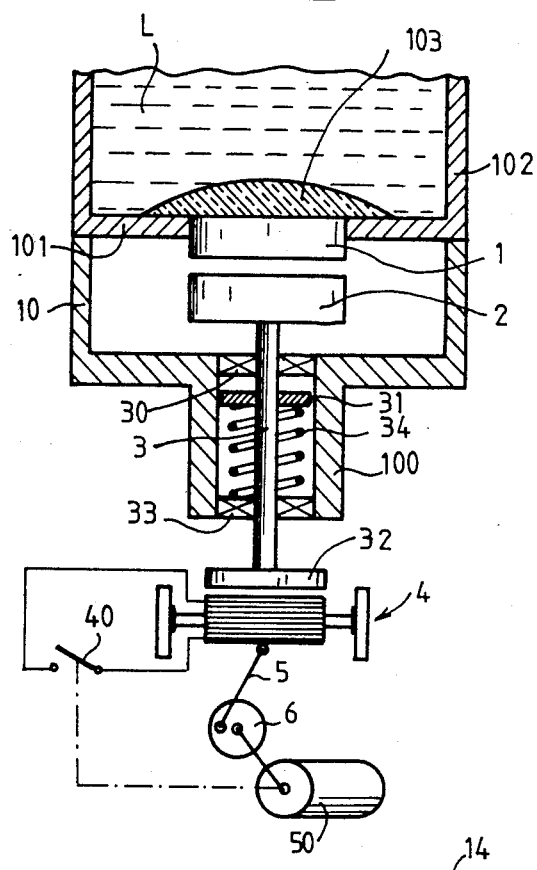
FIG. 1 shows schematically a first embodiment of an impact elastic pulse generator of the invention.

In FIG. 1 an anvil 1 is shown surrounded by a collar 101 fixed to a cylindrical support 10 and cooperating with a hammer 2 itself fixed to one end of a rod 3 which slides in two ball bearings 30–33 mounted in a sleeve 100 which extends from the bottom of the cylindrical support 10. At the other end of rod 3, externally of sleeve 100, is fixed the armature 32 of an electromagnet 4. The yoke of the electromagnet is mounted for sliding along the axis of the rod.

It is driven with a reciprocal translational movement by a link-crank system 5–6, itself actuated by a motor 50. A switch 40 controls the switching on of the electromagnet. A broken line symbolizes the control of this switch by the shaft of the motor, through a cam. A compression spring 34 bears on stop 31 integral with the rod in the vicinity of bearing 30 and on bearing 33.

On the face of anvil 1 opposite that which cooperates with hammer 2 is fixed a lens 103 adapted for transforming the flat elastic wave generated by the impact of the hammer into a spherical wave which is propagated in a liquid L contained in a tank 102 whose bottom is formed by the collar 101.

On switching on the device, with the hammer applied against the anvil by spring 34, the motor 50 drives the yoke of the electromagnet into the high position, in which it is in contact with the armature 32. At this moment, the cam closes the switch so that the electromagnet is energized and, with the yoke now moving downwards, the armature is driven by it in this movement. Spring 34 is thus compressed. At the end of an adjustable travel distance, the cam opens the switch so that the electro-magnet frees its armature and so that the spring then drives the hammer until it strikes the anvil.

The spherical wave generated converges at the focal point of the lens where a considerable concentration of energy is formed.

By way of example, if the hammer and the anvil are made from steel, for an impact speed of 10 m/s, the pressure generated will be $2.10^8$ Pa.

As will be mentioned further on, an impedance matching layer is advantageously provided between the anvil and the liquid; we may then consider that about a tenth of the pressure generated will be transmitted to the liquid. The lens concentrates the pressure at the focal point in a factor 10 for example, which gives a pressure of 2 kbar at the focal spot.

This pressure increases linearly with the impact speed and its transmission may be further improved by multiplying the impedance matching layers.

An impact speed of 10 meters per second is easy to obtain. By way of example, for a total moving mass of 0.1 kg, a distance travelled of 10 cm and a force of 100 Newtons, the speed will be 14 meters per second.

A factor of concentration of the pressure at the focal point of 10 is itself obtained without difficulty. In fact, for an elastic pulse of a duration of 1 microsecond, the diameter of the focal spot will be of the order of 3 mm. If the anvil has a diameter of 5 cm, the factor of multiplication of the pressure is 16.66.

It should however be pointed out that the above calculations are only valid if all the points of the surfaces which enter into contact do so strictly simultaneously, failing which the wave ceases to be flat and can no longer be focused, so that duration of the pulse increases, whereas its intensity drops relatively rapidly. Thus, in order to obtain a rising front of 1 microsecond, with a speed of 10 m/s, the tolerance of inherent flatness and of parallelism of the cooperating surfaces will be of the order of $\mp 5$ microns.

Such inherent flatness may be obtained with parts made from steel treated by optical polishing, but the parallelism is on the other hand difficult to adjust and especially to maintain during operation.

It is possible, for example, by mounting the hammer on a ball and socket joint and by locking the joint after application of the hammer, to obtain at the outset a strict parallelism better than 1 micron.

To guarantee that this parallelism is kept despite the considerable stresses undergone by the device during operation thereof, an automatic correction device will be preferably used (it is however not indispensable).

Figure 2:
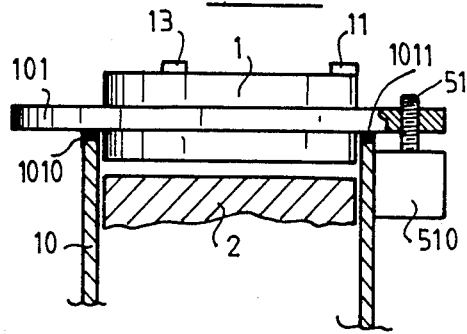
FIGS. 2 and 3 show, respectively in elevation with partial section and in a top view, a method of mounting the anvil on its support.
Figure 3:
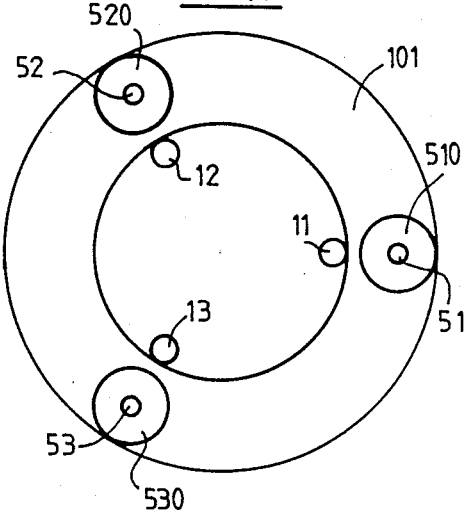

In FIGS. 2 and 3 the anvil 1 has been shown surrounded by the collar 101. The lower surface of this collar is fixed by resilient low compliance supports 1010-1011 (of the silent block type) on the edge of the cylindrical support 10. The position of the plane of the collar with respect to the horizontal plane may be adjusted by means of three precision screws 51-52-53 controlled by motors 510-520-530. Three sensors 11-12-13, for example of the piezoelectric or stress gauge type, are fixed to the periphery of the anvil, on the face thereof in contact with the lens (this latter has not been shown), facing the respective adjustment screws. These sensors detect the arrival, on said transmission face of the anvil, of the pressure wave generated by the impact on the opposite impact face. If the hammer and the anvil are not strictly parallel, the leading edges of the pulses arrive at the three sensors at times offset with respect to each other.

Figure 4:
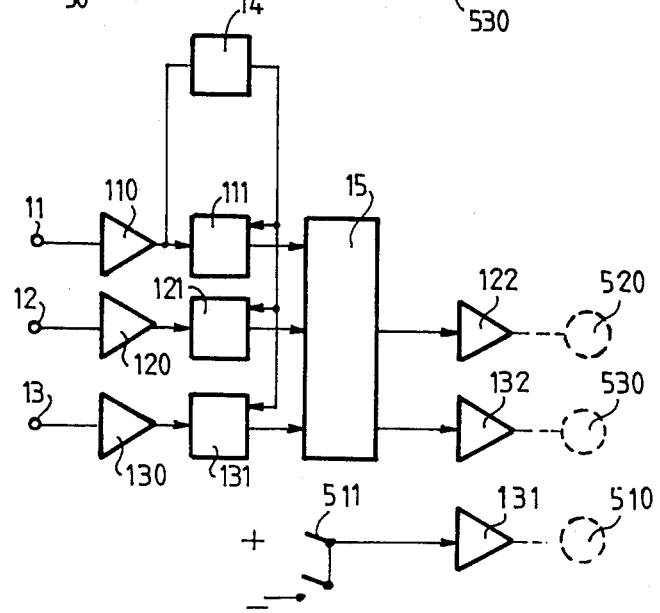
FIGS. 4 and 5 show a circuit for automatically adjusting the parallelism of the associated faces of the hammer and of the anvil.

In FIG. 4 has been shown a circuit comprising three amplifiers 110-120-130 which receive the signals of the respective sensors. The leading edge of these signals triggers flip flops 111-121-131. A monostable multivibrator 14 triggered by the output of one of the amplifiers, 110 for example, resets the flip flop simultaneously a given time after the impact. Thus rectangular waves are obtained, of variable width, which are applied to a logic circuit 15 adapted for comparing the width of the rectangular waves coming from the flip flops 121 and 131 with that of the rectangular wave supplied by flip flop 111, taken as reference and delivering signals proportional to the differences of width. These signals, amplified at 122, 132, serve for controlling the motors 520-530 in the forward or reverse direction of rotation depending on the sign of the differences.

The parallelism correction is thus carried out progressively during each of the successive impacts and is held permanently after a certain time. Motor 510, controlled through an amplifier 131 from an energization source which is connected thereto through a switch 511, is controlled manually, in the forward or reverse direction, for varying the mean position of the anvil. The advantage of this mean position adjustment will appear in the following.

Figure 5:
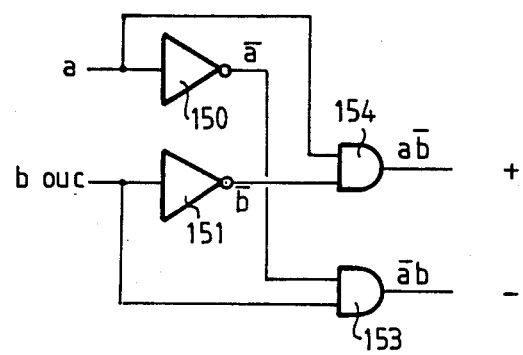

In FIG. 5 a logic circuit has been shown comprising two logic inverters 150 and 151 which receive respectively the signal a coming from flip flop 111 (FIG. 4) and one of the two signals, for example b, coming from flip flops 121 and 131. The output signals $\bar{a}$ and $\bar{b}$ of these inverters are applied to two AND gates 153 and 154 which receive moreover b respectively a and thus generate the respective logic products $\bar{a}b$ and $a\bar{b}$.

Figure 6:
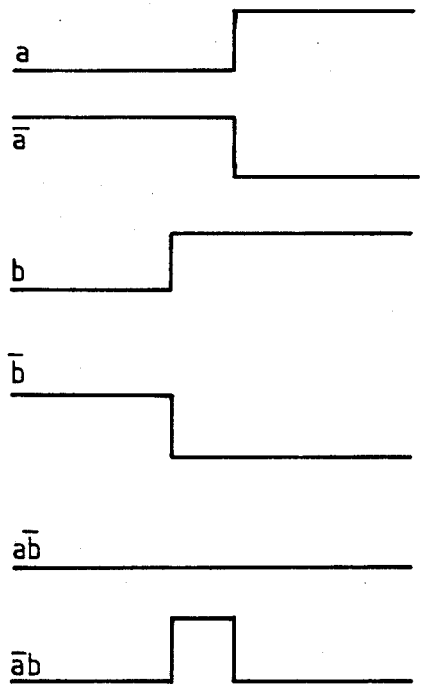
FIGS. 6 and 7 show the wave forms of the signals at different points of the adjustment circuit.
Figure 7:
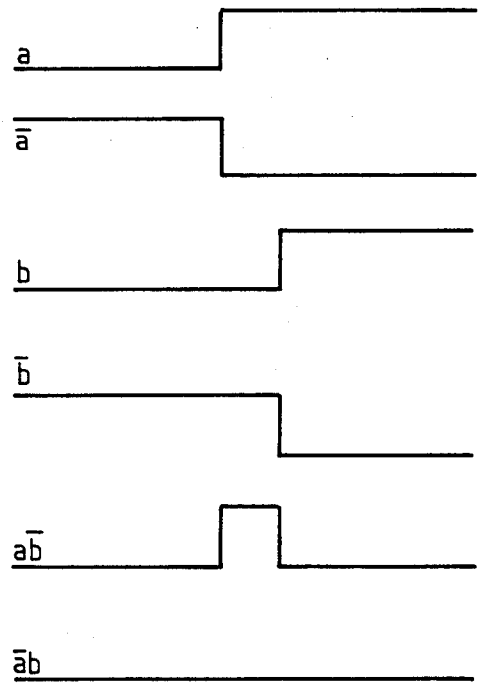

FIG. 6 shows the signals a, $\bar{a}$, $\bar{b}$, $a\bar{b}$, and $\bar{a}b$ when b is ahead of a and FIG. 7 shows the same signals whan b is behind a.

In the first case, the output $\bar{a}b$ is positive, whereas the output $a\bar{b}$ is zero, and it is the reverse in the second case. Thus motor 520 can be controlled in the forward or reverse direction with the two outputs from gates 153 and 154. An identical circuit, in which the inverter 151 will receive the signal c from flip flop 131, will control the motor 530.

Figure 8:
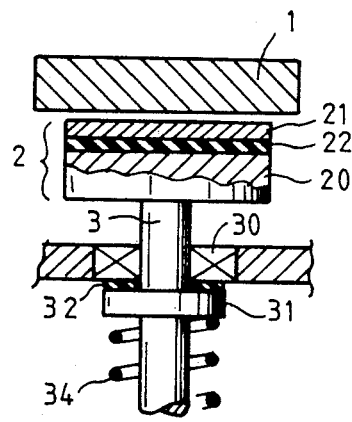
FIG. 8 shows a preferred embodiment of the hammer and of its drive rod.

Besides the first problem mentioned above of maintaining the parallelism between the anvil and the hammer, a second problem arises, namely the permanent deformation of the parts which risks occurring if the stress is applied for too long a time. In order to reduce the contact time between hammer and anvil to the value strictly necessary for generating the elastic wave front, the device illustrated in FIG. 8 is advantageously used. The hammer 2 is formed by a solid piece 20, preferably made from a light alloy, to which is fixed a steel plate 21 having, for example, a thickness of 3 mm, with interpositioning of a resilient layer 22. Stop 31, in the form of a collar, bears at the end of travel on bearing 30 through a resilient seal 32 intended to prevent instantaneous blocking of the hammer. In this rest position the external face of plate 21 of the hammer is very close to the anvil (by construction of the device and by adjustment of the mean position of the anvil), at the limit of contact (a few hundredths of a millimeter for example). At the end of travel of rod 3, the solid part 20 of the hammer, which arrives at high speed, is therefore blocked (within one or two millimeters of movement by the cooperation of stops 30–31 just before striking the anvil. But plate 21, because of the resilience of layer 22, continues to advance by inertia over a very short distance. A pressure wave is then propagated in the anvil 1 and in plate 21 and is reflected from the internal face of plate 21, because of the fact that the impedance of said plate is much higher than that of the resilient layer 22.

This reflected wave cancels out the incident pressure, after a time corresponding to an outgoing and return travel of the elastic wave in plate 21, at the end of which the pressure at the level of the anvil is thus cancelled out.

This effect, combined with the return force of the elastic layer, causes rupture of the contact between the hammer and the anvil.

In plate 21 of the above example, the outgoing and return travel time is of the order of 1 microsecond, that is to say equal to the theoretic duration of formation of the wave front. The static stresses are practically eliminated.

Figure 9:
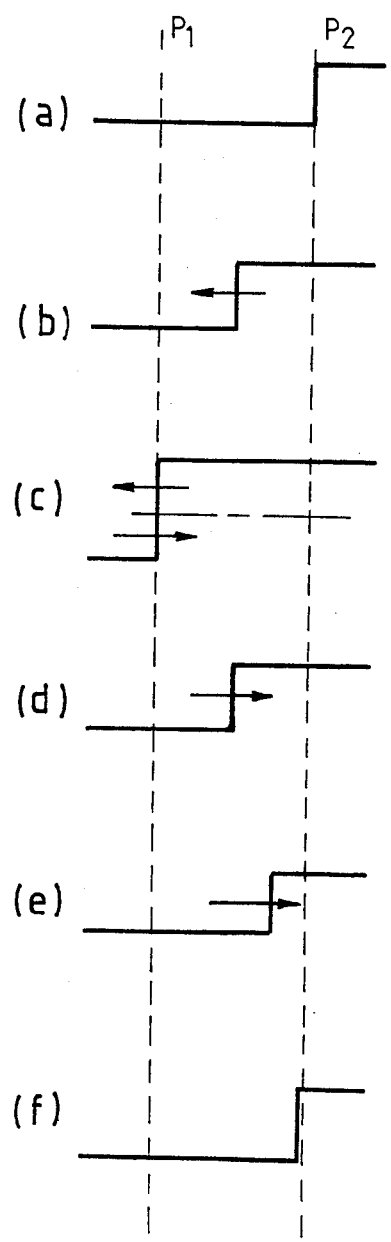
FIG. 9 illustrates the evolution of the pressure wave in the impacting plate of the hammer of FIG. 8.

FIG. 9 illustrates the propagation of the pressure wave P inside the plate 21 after impact. $P_1$ is the pressure on the rear (or external) face, $P_2$ the pressure on the front face.

At (a) has been illustrated the moment of impact; at (b) to (f) times subsequent to the impact, respectively by 0.25 μs; 0.5 μs (moment of reflection from the rear face); 0.75 μs, 0.9 μs and 1 μs.

A third problem in constructing the elastic wave generator described is that of aerodynamic damping: just before the impact, a vane of air is imprisoned between the hammer and the anvil and may cause considerable braking. To attenuate this effect, the support assembly for the hammer will be placed in a vacuum enclosure, or more simply a multitude of air discharge furrows will be formed in the anvil or the hammer.

A fourth problem is that of the transmission of the energy of the liquid. The impedance of steel, where the wave is generated, is about 30 times greater than that of water and impedance matching plates are required if it is desired to transmit an appreciable fraction of the energy. Several plates will be advantageously interposed between the material of the anvil and the water, with staggered impedances and a thickness equal to a quarter of the wave length of the pulse.

The construction of such impedance matching plates is within the scope of a man versed in the art.

In order to act efficiently on a localized obstacle, such as a renal calculus, it is useful to locate it with precision with respect to the spherical focal spot and to visualize the real position of this latter.

Figure 10:
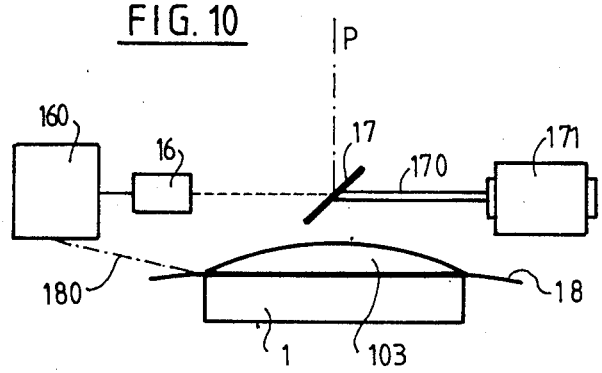
FIGS. 10 to 12 show schematically means for visualizing the obstacle at which the generator is aimed and the focal spot of the elastic wave beam generated.
Figure 11:
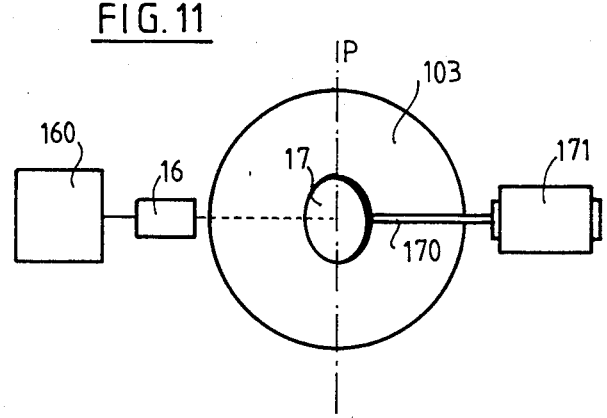
Figure 12:
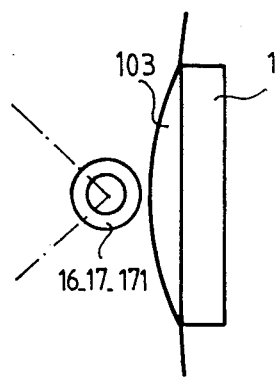

In FIGS. 10 to 12, the elastic wave generator has been symbolized by the anvil 1 fixed to an acoustic lens 103; an echograph probe 16 cooperates with a mirror 17 oriented at 45° which oscillates about a shaft 170 in the Figure, driven by a motor 171.

The ultrasonic beam generated by probe 16 (associated, of course, with an appropriate electric pulse emitter which forms part of an echograph device shown symbolically by the rectangle 160), thus effects a sectorial scan in a plane P perpendicular to the plane of the FIGS. 10 and 11 and passing through the axis of symmetry of the elastic wave generator (FIG. 12). Device 160 comprises means—known per se—for receiving and displaying the echoes formed on the target. Thus the display of the obstacle is obtained.

Mirror 17 may have a diameter of only 10 mm, for example, so as to intercept only a small part of the acoustic energy emitted by the elastic wave generator.

With such a device, it is possible to further visualise the focal spot of the elastic wave beam generated. For this, a thin sheet of a piezoelectric polymer of "$PVF_2$" (18, FIG. 10) is bonded to the surface of the anvil and it is connected (which is symbolized by the broken line 180) to the echograph device 160. Thus the emission of an echograph ultrasonic beam is obtained which will have the same geometrical structure as the elastic wave beam generated by the anvil, but of course, a much lower power and a much higher pulse rate.

It will be noted that the $PVF_2$ sheet has an impedance close to that of water and does not hinder the propagation of the pressure wave produced by the anvil. This material, slightly resilient, is very resistant and may withstand the passage of the pressure wave without damage.

The $PVF_2$ sheet further allows the shape of the pressure pulse to be controlled.

Figure 13:
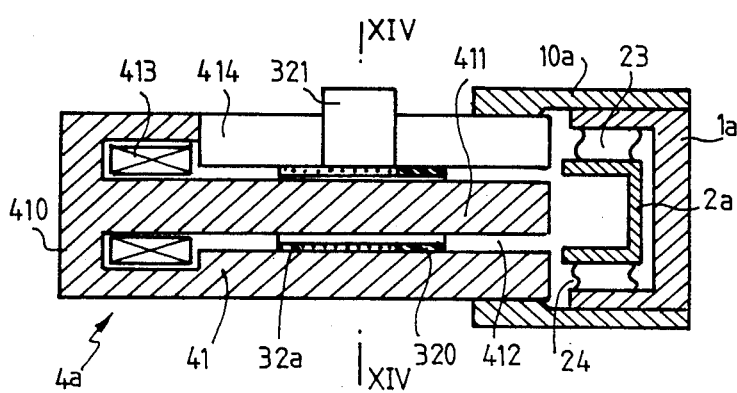
FIGS. 13 and 14 show respectively in longitudinal section and in cross section a second embodiment of the generator.
Figure 14:
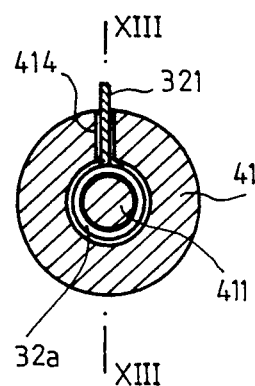

In FIGS. 13 and 14, a variant of construction has been shown in which the hammer 2a is formed by a cylindrical hollow cup of a few millimeters in thickness which cooperates with an anvil of the same form 1a surrounded by a sleeve 10a, extending beyond the anvil for serving as means supporting and centering the cylindrical yoke of an electromagnet, designated as a whole by the reference number 4a. This yoke comprises an external hollow cylindrical part 41 closed at one end by a bottom 410 extended by a cylindrical axial core 411. This latter forms an air gap 412 with the piece 41 and defines, with the bottom and a portion of smaller thickness of piece 41, an annular housing for a coil 413 which is permanently supplied with power.

Piece 41, core 411 and the cylindrical cups 1a and 2d have their axes of symmetry merging and the annular edge of hammer 2a is disposed opposite the annular air gap 412 so that a cylindrical assembly (mounted for sliding about the core 411 in the air gap and formed by a mobile cylindrical piece 32a extended by a resilient stop 320) may impact on the edge of the hammer.

The hammer is attached to the anvil by means of two metal resilient disks 23-24 having circular undulations which allow the hammer to move by a few millimeters in the axis of the device, while ensuring strict lateral guidance.

The cylindrical piece 32a is rigid and comprises a coil fed with pulses by flexible conductors, not shown, whereas stop 320 is slightly resilient. It is made for example from rubber or silicon. This assembly is relatively light with respect to the weight of the hammer.

The hollow cylindrical piece 41 has a slit 414 open along two outer and inner generatrices for housing a plate 321 integral with the cylindrical piece 3 and allowing said plate to slide parallel to said generatrices. This plate prevents the assembly 32a-320 from rotating when it is propelled by the action of the field of the electromagnet on the current which flows through the coil (current pulse of 1/100 second, for example, having a suitable polarity for driving said assembly into the impact position and a reverse polarity for driving it into the rest position).

At the outset, assembly 32a-320 is in the rest position. The hammer 2a is then situated at about 5 mm from the anvil 1a for example.

A pulse applied to coil 32a projects this latter towards the right.

At the end of travel, stop 320 comes into contact with the hammer and transmits thereto the kinetic energy of piece 32a, within a time of the order of a few milliseconds. The energy transfer must be completed before the hammer comes into contact with the anvil. The transfer time will be determined by the resilience and the size of the stop. This latter is adjusted so as to prevent bouncing before transfer.

The transfer of energy between the hammer and the anvil only lasts a few microseconds. Since the transfer of energy between piece 32a and the hammer takes a time about a thousand times greater, the pressures generated between said piece and hammer are much smaller than those of the hammer-anvil impact.

The result is that the fatigue of the propulsion device is limited.

It will be noted that the peak pressure of the elastic wave generated only depends on the speed of the hammer (and not its mass), whereas the duration thereof depends on its thickness (outgoing and return travel of the wave in the hammer). With the solution described in FIG. 13, the impact speed may reach 30 m/sec.

The whole of the mechanism described is advantageously housed in an air evacuated enclosure, so as to limit the friction and especially the aerodynamic damping of the final impact.

The pressure generated may be adjusted by adjusting the intensity of the current flowing through coil 32a. The speed of movement of this coil may be estimated at all times with precision—for controlling it—by measuring the counter—electromotive force induced at its terminals.

It should be understood that the two embodiments described and shown are not limitative. The cooperating surfaces of the hammer and of the anvil are not necessarily equal, nor even flat, and the emitting surface of the anvil could have a shape appropriate for focusing the beam.

Moreover, other means for uncoupling the impacting plate (21, FIG. 8 or 13), which necessarily has a simple geometrical shape, from the propelling device properly speaking (which comprises, in FIG. 8, the main mass 20 of the hammer) as soon as the kinetic drive energy has been transferred to said impacting plate, may be thought up. They will not necessarily comprise a resilient element (such as 22, FIG. 8 or 320, FIG. 13)

What is important finally is above all that the reflected wave should not propagate in the propelling assembly, which it would fatigue rapidly, and which necessarily has weak points, its structure being relatively complex and that the transfer of energy to the impacting piece is much longer than the transfer of energy from the impacting piece to the anvil.

What is claimed is:

1. The assembly of a high power high frequency elastic pulse generator having an elastic wave radiating surface and a liquid containing enclosure having a wall surface portion in which said elastic wave radiating surface is rigidly mounted for propagating elastic waves within the liquid, wherein said pulse generator comprises:
   i. an anvil having said radiating surface and an impact surface opposite said radiating surface and at a distance therefrom;
   ii. a hammer comprising a thrust part and an impact part of a thickness substantially lower than said thrust part, said impact part having an outer impact surface facing said impact surface of the anvil and parallel thereto;
   iii. and actuating means for periodically propelling and returning the hammer alternately at said high frequency to bring the hammer to an active position of cooperation with the anvil and return it to a rest position far from the anvil, said actuating means comprising means for propelling the thrust part from the rest position to the active position then stopping the thrust part in the active position in which said outer impact surface of the impact part does not engage the impact surface of the anvil and immediately returning the thrust part towards its rest position while the impact part moves towards the anvil until engagement of the impact surface thereof with the impact surface of the anvil and
   iv. resetting means for disengaging the impact part from the anvil immediately after said engagement.

2. The assembly as claimed in claim 1 wherein said actuating means are adapted for propelling the thrust part at a speed of the order of ten meters per second and said impact surfaces are at a distance less than ten hundredths of a millimeter when the hammer is in its active position.

3. The assembly as claimed in claim 1, wherein said parallel impact surfaces are flat, their inherent flatness and their parallelism being provided with tolerences less than ten microns.

4. The assembly as claimed in claim 1, wherein said assembly further comprises sensors mounted for detecting the pressure wave fronts at respective points points distributed at the periphery of said radiating surface; means for measuring the time shifts between the respective wave fronts received by the respective sensors; control means for adjusting the parallelism of said impacting surfaces and means for setting said control means, as a function of the time shifts thus measured.

5. The assembly as claimed in claim 1, wherein said thrust part is a solid block, said impact part is a plate of a few millimeters in thickness, said resetting means consist of a resilient layer which connects said plate to said block and said actuating means comprise a rod integral with said block and comprising a shoulder which bears against a fixed stop through a resilient layer when the hammer is in its active position.

6. The assembly as claimed in claim 1, further comprising an acoustic lens mounted on said wall surface portion and coupled to said radiating surface and at least one impedance matching plate interposed between said radiating surface and said lens.

7. The assembly as claimed in claim 6, said assembly further comprising means for focussing the elastic wave beam radiated from said radiating surface onto a target and echographic means for displaying an image of said target.

8. The assembly as claimed in claim 7, said assembly further comprising a sheet of a piezoelectric polymer bonded to said radiating surface and connected to said echographic means.

9. The assembly as claimed in claim 1, wherein said thrust part is freely movable with respect to the impact part, the anvil is cup-shaped and has a bottom forming the impact surface and the radiating surface thereof and a cylindrical wall portion and said resetting means comprise means for resiliently coupling the impact part to the cylindrical portion of the anvil.

10. The assembly as claimed in claim 9, wherein said thrust part is propelled by electrodynamic actuating means and comprises a relatively resilient portion adapted for engagement with the impact part.

* * * * *